US010597688B2

(12) United States Patent
Yu et al.

(10) Patent No.: US 10,597,688 B2
(45) Date of Patent: Mar. 24, 2020

(54) METHOD FOR PREPARING FERMENTABLE SUGAR FROM WOOD-BASED BIOMASS

(71) Applicant: KOREA RESEARCH INSTITUTE OF CHEMICAL TECHNOLOGY, Daejeon (KR)

(72) Inventors: Ju Hyun Yu, Daejeon (KR); Chan Duck Jung, Daejeon (KR); Seung Hwan Lee, Daejeon (KR); In-Chul Kim, Daejeon (KR); Kyung Sik Hong, Daejeon (KR); In Yong Eom, Daejeon (KR); Jong Geon Jegal, Daejeon (KR); Bong Keun Song, Daejeon (KR)

(73) Assignee: Korea Research Institute of Chemical Technology, Yuseong-gu, Daejeon (KR)

( * ) Notice: Subject to any disclaimer, the term of this patent is extended or adjusted under 35 U.S.C. 154(b) by 59 days.

(21) Appl. No.: 14/655,158

(22) PCT Filed: Dec. 26, 2013

(86) PCT No.: PCT/KR2013/012202
§ 371 (c)(1),
(2) Date: Jun. 24, 2015

(87) PCT Pub. No.: WO2014/104755
PCT Pub. Date: Jul. 3, 2014

(65) Prior Publication Data
US 2015/0353977 A1    Dec. 10, 2015

(30) Foreign Application Priority Data

Dec. 28, 2012    (KR) ........................ 10-2012-0156000

(51) Int. Cl.
*C12P 19/02* (2006.01)
*C12P 19/14* (2006.01)
*C12N 1/20* (2006.01)

(52) U.S. Cl.
CPC ............... *C12P 19/02* (2013.01); *C12N 1/20* (2013.01); *C12P 19/14* (2013.01); *C12P 2201/00* (2013.01)

(58) Field of Classification Search
None
See application file for complete search history.

(56) References Cited

U.S. PATENT DOCUMENTS

2002/0164731 A1*  11/2002  Eroma ...................... C12P 7/10
                                                          435/163
2004/0231661 A1*  11/2004  Griffin ..................... C12P 7/10
                                                          127/1
2009/0061495 A1    3/2009  Beatty et al.
2011/0300586 A1   12/2011  Liu et al.
2012/0231147 A1*   9/2012  Srinivasan ................ A23L 5/20
                                                          426/618
2015/0353977 A1   12/2015  Yu et al.

FOREIGN PATENT DOCUMENTS

KR    20090111037 A    10/2009
KR    2011-0040367 A    4/2011
KR       101036853 B1    5/2011
KR    20120073087 A    7/2012
WO     2012/087068 A2   6/2012

OTHER PUBLICATIONS

Kumar et al., Ind. Eng. Chem. Res. 48(8): 3713-3729 (2009).*
Pérez et al., Fuel 87: 3640-3647 (2008).*
Dr. Michael E Himmel; "Biomass Recalcitrance Deconstructing the Plant Cell Wall for Bioenergy", Blackwell Publishing; Published Online: Mar. 3, 2009; 17 pages
Jan Larsen, et al; "Inbicon makes lignocellulosic ethanol a commercial reality", Biomass and Bioenergy; vol. 46, pp. 36-45; Available online Apr. 20, 2012.
Run-Cang Sun; "Cereal Straw as a Resource for Sustainable Biomaterials and Biofuels", 1st Edition, Chemistry, Extractives, Lignins, Hemicelluloses and Cellulose, 1 page from Chapter 2 of the book. Release Date Mar. 17, 2010.
M.L.M Villarreal, et al; Detoxification procedures of eucalyptus hemicellulose hydrolysate for xylitol production by Candida guilliermondii; Enzyme and Microbial Technology; vol. 40, Issue 1, pp. 17-24; Dec. 6, 2006.
International Search Report dated Apr. 14, 2014; PCT/KR2013/012202.
Xu, Y., et al.; "Integrating starchy substrate into cellulosic ethanol production to boost ethanol titers and yields", Applied Energy 195 (2017) 196-203.
Hu, Z., et al.; "Enhancing enzymatic digestibility of switchgrass by microwave-assisted alkali pretreatment", Biochemical Engineering Journal 38 (2008) 369-378.
Persson, T., et al.; "Fractionation of wheat and barley straw to access high-molecular-mass hemicelluloses prior to ethanol production", Bioresource Technology 100 (2009) 3906-3913.

(Continued)

*Primary Examiner* — Erin M. Bowers
(74) *Attorney, Agent, or Firm* — Harness, Dickey & Pierce, P.L.C.

(57) ABSTRACT

The present invention relates to a method for preparing, from wood-based biomass, a high concentration of fermentable sugar which can be effectively used in culturing various industrial fermented bacteria. According to the method of the present invention, biomass can be extracted by hot water prior to a pre-treatment so as to remove extractible substances such as mineral salts to thus minimize the content of impurities in raw materials for an enzymatic saccharification. The biomass from which substances extractible by hot water are removed is pre-treated in the condition where xylan yield rate is maximized, thus achieving maximum inhibition of the generation of over-decomposed products of sugar. Subsequently, fermentable sugar for culturing various industrial fermented bacteria can be prepared in an inexpensive manner by only concentrating, using a separator membrane, the sugar solution obtained by an enzymatic saccharification of the pre-treated solid content obtained by a solid-liquid separation without washing the solid content with water.

6 Claims, No Drawings

(56) References Cited

OTHER PUBLICATIONS

Aguilar, D. L., et al.; "Scale-up and evaluation of hydrothermal pretreatment in isothermal and non-isothermal regimen for bioethanol production using agave bagasse", Bioresource Technology 263 (2018) 112-119.
Xu, Y., et al.; "Modified Simultaneous Saccharification and Fermentation to Enhance Bioethanol Titers and Yields", Fuel 215 (2018) 647-654.

* cited by examiner

METHOD FOR PREPARING FERMENTABLE SUGAR FROM WOOD-BASED BIOMASS

FIELD OF THE INVENTION

The present invention relates to a method for preparing fermentable sugar from lignocellulosic biomass in high yields which can be effectively used in culturing various industrial strains for fermentation.

BACKGROUND OF THE INVENTION

In recent years, significant research efforts have been made worldwide to develop transportation fuels and industrial chemicals from sustainable biomass to effectively deal with the depletion of fossil fuel and global warming caused by greenhouse gases.

Biomass comprises lignocellulosic biomass, which mainly includes phanerophytes, and algal biomass, which mainly includes algae growing in water. Cellulose, one of the structural components that constitute biomass, is an abundant resource which takes up 20% to 50% of biomass, and is also a highly polymerized condensation product of glucose, which is considered as a primary nutrient for fermentation strains. Thus, numerous research and development efforts have focused on mass production of highly purified glucose from cellulose.

In addition to cellulose, however, lignocellulosic biomass also contains hemi-cellulose (about 15 to 35%), which is prone to over-decomposition, and lignin (about 10 to 30%), which is difficult to be reduced due to its complex structure. Additionally, lignocellulosic biomass also contains water-extractable substances including water-soluble starch, free sugars, proteins, pectin, tannin, various alkaloids, organic acids, various inorganic salts, and the like. Generally, such ingredients are contained slightly less in quantity: 20 to 30% in grassy biomass and 5 to 20% in woody biomass (see Michael E. Himmel (2009) Biomass recalcitrance, Blackwell Publishing; Run-Cang Sun (2010) Cereal Straw as a Resource for Sustainable Biomaterials and Biofuels, Elsevier).

Among the extractable substances contained in lignocellulosic biomass, starch or free sugar can be used in the process of producing fermentable sugars. The rest of the ingredients, however, not only act as impurities but may also deteriorate the rate of sugar yield during the production of fermentable sugars, and thus, it is important to recover or remove these ingredients.

Korean Laid-open Patent Publication No. 2011-0040367 discloses equipment that discharges liquid material, as a process of continuous fractionation of biomass, by introducing hot water into a reactor, stirring the mixture for a certain period, and then discharging a liquid material using vapor pressure. Although this prior art was designed to extract hot water-extractable substances by using the equipment, it was not suitable for removing the extractable substances because the extraction of liquid material through valves does not take place sufficiently under high pressure, and the total recovery rate was merely 50% or lower, which was very low even after repeating the fractionation and recovery processes several times due to the tunneling effect of the contents during the extraction process.

Inbicon A/S discloses a method for removing extractable substances from biomass by subjecting the biomass to autohydrolysis, removing a liquid material containing a large amount of ingredients that inhibits microbial activity via solid-liquid separation, and then washing the pretreated solid residue with water (see Jan Larsen et al., 2012, Biomass and Bioenergy, 46, 36-45). Although this method has an advantage in that it yields clean pretreated solid residues which can be used for production of high quality fermentable sugar, it has a downside that an increase in manufacturing cost is inevitable due to solid-liquid separation and repeated washing processes. Also, an additional process of adding a certain amount of the pretreated liquid material containing microbial growth inhibitors is required to prevent possible contamination which can be caused by lactic acid bacteria during enzymatic saccharification or alcohol fermentation. For this reason, the contents of the resulting product would become more complex after going through a reaction under high temperature and high pressure conditions and, as a result, the resulting product is added with unknown extractable substances from the biomass. Moreover, the liquid material is obtained as a byproduct from the pretreatment of biomass can only be used for production of low-value products, e.g., fertilizers, and cannot be developed as a value-added product due to the presence of xylose and xylan, as well as over-decomposed products of sugar such as furfural, HMF and the like; protein denaturants generated by Maillard reaction at a high temperature of, for example, 190° C.; various organic acids; lignin degradation products; and various inorganic salts.

In the process of manufacturing glucose from biomass, pretreatment process and saccharification process generally take place consecutively because cellulose is not easily converted to glucose when the biomass is merely in a pulverized form. The pretreatment of biomass refers to a process of treating pulverized or crushed biomass in a physicochemical manner so as to make each structural component of the biomass suitable for fractionation. The saccharification of biomass refers to a process of converting a pretreated cellulose, which has become suitable for more efficient hydrolysis because hemicellulose or lignin that surrounds cellulose has been partially or wholly decomposed or dissolved, to glucose in a physicochemical or biochemical manner.

Examples of conventional methods used in the pretreatment of biomass include autohydrolysis (or hydrothermolysis), dilute acid pretreatment, lime pretreatment, ammonia pretreatment (ARP, etc.), steam explosion and etc. The pretreatment process renders cellulose more reactive towards hydrolyzing enzymes by mostly dissolving hemicellulose or lignin contained in the biomass. Not only do the type of biomass and the reaction conditions heavily affect the efficiency of the pretreatment, these factors also change the types and amounts of compounds other than sugar produced in the saccharification process. Recently, among these examples, autohydrolysis is getting more attention because it provides an economic advantage owing to its simple process and also has wide applicability towards various kinds of biomass.

The enzymatic hydrolysis of the pretreated material refers to a process of converting cellulose contained in the pretreated biomass, which has been converted into a form that can easily react with enzymes, to glucose by treating with cellulases. Depending on the pretreatment method selected, the cellulases used in the enzymatic hydrolysis may further include a variety of enzymes, e.g., hemicellulose, amylase, pectinesterase, and the like, to promote hydrolysis reaction.

After the pretreatment and saccharification processes, the sugar-containing materials obtained from lignocellulosic biomass can be further treated in accordance with two major methods. First, there is a method called simultaneous saccharification and co-fermentation in which a saccharified material (hereinafter referred to as "saccharified material") containing the residue obtained from saccharification process (hereinafter referred to as "hydrolysis residue"), or after conducting saccharification process, the pretreated material containing a small amount of glucose is directly added with fermentation strains and additives, and which is then subjected to fermentation. Currently, this method has been widely used in studies and empirical manufacturing of bio-alcohols. According to the second method, a sugar solution is prepared via solid-liquid separation after the saccharification has been completed, and then such sugar solution is used as a fermentable sugar.

When a sugar solution is prepared from lignocellulosic biomass via physicochemical pretreatment and enzymatic hydrolysis, the sugar solution contains not only monosaccharides such as glucose but also a number of impurities. Representative examples of the impurities include overdecomposed products of sugar such as aldehydes including furfural and hydroxymethylfurfural (hereinafter referred to as "HMF"), organic acids such as levulinic acid and formic acid, and alcohols such as methanol; as well as hydrolysate of hemicellulose including acetic acids, and hydrolysate of lignin including various phenolic compounds. Depending on the kind of fermentation strain, these impurities may act as a microbial growth inhibitor or metabolite production inhibitor. It has been reported that phenolic compounds, i.e., hydrolysate of lignin, contained in a sugar solution is the most powerful microbial inhibitor; furfural and HMF may act as a selective inhibitor depending on their concentrations; and many kinds of acids such as acetic acid exhibit different physiological reaction depending on the strain. Accordingly, attempts have been made to minimize the effects caused by various impurities or to use the saccharified material from biomass directly for microbial fermentation by improving fermentation strain using molecular biology techniques and selecting suitable microbes from new stains. Yeasts, an ethanologen, are known to be the most resistant strain against microbial inhibitors, and recently studies have focused on modifying such strain for manufacturing of bio-alcohols from a lignocellulosic sugar solution.

On the other hand, microbial growth or metabolite production of most of the industrial microbes such as *Escherichia coli* or *Clostridium acetobutylicum* can be greatly hindered by certain impurities. Accordingly, various studies have been conducted, e.g., overliming and polymerization using lignin peroxidase, and the like, so as to detoxify microbial inhibitors contained in sugar solutions obtained from lignocellulosic biomass. Also, an attempt has been made to eliminate such inhibitors by applying different chromatography techniques using adsorption and partition (see Villarreal, M. L. M. et al., Enzyme and Microbial Technology, 40, 17-24, 2006).

Meanwhile, in order to minimize the amount of microbial inhibitor contained in sugar solutions, pretreated biomass may be washed prior to enzymatic saccharification. This technique, however, may cause an undesirable microbial contamination, e.g., *L. acidophilus*, during the enzymatic saccharification or alcohol fermentation process after the pretreated material has been washed, and thus, some of the pretreated liquid material can be added back in order to avoid such contamination. Although this technique is very useful for alcohol fermentation which employs yeast that is resistant to microbial inhibitors because microbial inhibitors such as acetic acid and phenolic compounds are released from the pretreated biomass as the enzymatic saccharification and ethanol fermentation proceed. However, no application utilizing this technique in the manufacturing of fermentable sugar has been reported until now. Also, in case of pretreated biomass having a small average particle diameter due to pulverization or pretreatment, there is a risk of a decrease in the sugar yield since some of the particlized pretreated biomass may be lost during the washing process.

SUMMARY OF THE INVENTION

Accordingly, it is an object of the present invention to provide a method for preparing fermentable sugar from lignocellulosic biomass, utilizing a series of pretreatment and enzymatic saccharification processes for optimal sugar yield which minimizes the generation of microbial growth inhibitor and yields fermentable sugar in a high concentration for use as a fermentation medium.

In accordance with an aspect thereof, the present invention provides a method for preparing fermentable sugar from lignocellulosic biomass, which can be effectively used in fermentation of industrial microorganisms, comprising the steps of:

1) adding coarsely ground or powder lignocellulosic biomass with water, heating the mixture at 50 to 140° C. for 1 to 60 minutes, and then dewatering the mixture (hot water-extractable substance removal step);

2) adding water to the solid residue obtained in step 1), and pretreating the mixture at 170 to 210° C. for 1 to 30 minutes (autohydrolysis step);

3) subjecting the autohydrolyzed material obtained in step 2) to a solid-liquid separation to obtain a solid residue including a small amount of liquid part (solid-liquid separation step);

4) subjecting the solid residue obtained in step 3) to an enzymatic saccharification at a high temperature of 45 to 55° C. using a cellulase complex enzyme (enzymatic saccharification step);

5) repeating the solid-liquid separation and extraction using the saccharified material obtained in step 4) to yield a sugar solution (sugar solution recovery step); and 6) subjecting the sugar solution obtained in step 5) to filtration, concentration and then impurity removal (concentration step).

The method of the present invention can minimize the amount of impurities in the raw material for enzymatic saccharification by removing most of extractable substances such as proteins and inorganic salts through hot water extraction prior to pretreatment and, thus, can allow manufacturing of fermentable sugar for culturing various industrial fermentation strains by pretreating biomass, from which hot water-extractable substances have been removed, under conditions that hemicellulose sugar yield can be maximized and then concentrating the pretreated solid residue obtained by solid-liquid separation using a separation membrane without washing with water. Also, this method reduces purification costs owing to a decreased loading amount of impurities in the following purification process; maintains a high sugar yield due to the absence of cellulose loss caused by washing of the pretreated biomass prior to enzymatic saccharification; and allows preparation of fermentable sugar which is safe from undesirable microbial contamination such as lactic acid bacteria during the enzymatic saccharification owing to the presence of a minimal amount of microbial growth inhibitors and the enzymatic saccharification carried out at a high temperature. Further, the method can maximize the utilization efficiency of the biomass by separately recovering each of the hot water-extractable substances contained in the biomass and relatively pure liquid part containing xylooligosaccharides which can be used for manufacturing dietary fiber or xylitol.

DETAILED DESCRIPTION OF THE INVENTION

A method for preparing fermentable sugar of the present invention minimizes the amount of impurities including microbial inhibitors and the like by utilizing a series of steps including hot water-extractable substance removal step; autohydrolysis step; solid-liquid separation step; enzymatic saccharification step; sugar solution recovery step; and concentration step. Thus, such a method allows the production of fermentable sugar in high yields which can be effectively used in culturing various industrial fermentation strains.

In the first step of the present invention, i.e., the hot water-extractable substance removal step, coarsely ground or powder lignocellulosic biomass is added with water, heated at 50 to 140° C. for 1 to 60 minutes, and then water is removed from the mixture. This process not only improves the saccharification rate and sugar yield by minimizing the amount of substances which may act as a cellulase inhibitor during the enzymatic saccharification of the pretreated matter such as inorganic salts and the like that are included in grassy biomass in large quantity, but also lowers the manufacturing cost by reducing the loading amount of impurities in the purification process of the sugar solution after the enzymatic saccharification. Further, this process recovers and recycles useful materials that are contained in biomass as extractable substances such as starch and free sugars, proteins, lipids, pectin, tannin, alkaloids which exhibit various physiological activities, organic acids and inorganic acids; and it also lowers the possibilities for proteins to be converted to toxic materials via Maillard reaction or for other materials to be converted to undesirable compounds via reactions such as decomposition, condensation, modification, etc.

In the first step, biomass is immersed in water and then extractable substances may be recovered or removed by extracting the biomass with water at a temperature in which the water solubility is optimized. Preferably, an aqueous solution is removed by immersing the biomass, stirring the mixture at 50 to 105° C. for 1 to 60 minutes, and subjecting the mixture to a solid-liquid separation at a point where the elution of extractable substances is maximized before the mixture cools down. Most of the extractable substances contained in the biomass are removed during this process, and various kinds of extraction techniques may be used, for examples, counter-current extraction, co-current extraction, semi-batch type extraction and batch type extraction.

The purpose of this process is to extract and remove the maximum amount of extractable substances from the biomass using the minimum amount of hot water. In case of batch type extraction, a liquid material is removed by placing a pulverized biomass in an extractor, adding hot water thereto, extracting the mixture, and then subjecting the mixture to solid-liquid separation. During this process, the removal efficiency of the extractable substances can be improved with increase in the solid to liquid ratio (the ratio of biomass to water), which generally starts from about 1:4. For example, when 1 kg of biomass is added to 20 L of water, heated at 95° C. and subjected to solid-liquid separation to yield 3 kg of solid residues and 18 L of an aqueous solution, 90% of extractable substances are removed and only 10% is used for the following pretreatment process. In terms of biomass fractionation, however, the solid to liquid ratio is preferably 1:20 or less, in consideration of the cost of dewatering process for recycling the extracted substances as well as the water treatment costs. Thus, in the first step, the weight ratio of the coarsely ground or powder lignocellulosic biomass to water is, preferably, 1:4 to 1:20.

The removal efficiency of the extractable substances in biomass by hot water extraction can be improved as the extraction temperature and the solid-liquid separation temperature increase. This is because water solubilities of most substances increase as the temperature of water increases. Thus, in a preferred embodiment, the extraction and the solid-liquid separation is carried out in a range of 50 to 140° C., preferably, 80 to 105° C. Additionally, the immersion time may be shortened as the particle size of the biomass gets smaller. However, considering the energy cost of the pulverization as well as the counter-current extraction efficiency, the biomass is pulverized or crushed to have, preferably, an average particle diameter of 0.1 mm to 50 mm.

The water content of the solid residue after the extraction of extractable substances is in a range of, preferably, 50% to 90%, although it varies depending on the types of method and equipment used. After the extraction process, if necessary, a continuous centrifugal separator, a filter press, a drum filter or a screw press may be used to obtain solid residues in its most dewatered form.

In the second step of the present invention, i.e., the autohydrolysis pretreatment of the biomass, the generation of microbial inhibitors is minimized and the sugar yield is maximized; and this step is carried out by adding water to the pretreated substances and conducting the autohydrolysis under a condition that maximizes the sugar yield of hemicellulose such as xylose and xylan when all the pretreated substances are hydrolyzed enzymatically. In this step, the solid residues obtained from step 1) is added with water, and then pretreating the mixture at 170 to 210° C. for 1 to 30 minutes. The autohydrolysis pretreatment may be carried out by batch type or continuous pretreatment. The ratio of the solid residue amount to water used in the autohydrolysis, i.e., the solid to liquid ratio, is not specifically limited as long as the amount is sufficient to carry out the hydrolysis reaction of the biomass. However, considering the pretreatment efficiency and the fact that the microbial growth inhibitors generated during the pretreatment step will be carried over to the next step since the present invention omits washing of the pretreated substances after the pretreatment, the weight ratio of the solid residue to water is, preferably, 1:3 to 1:15. For example, in case of conducting batch type autohydrolysis using grassy biomass for the manufacture of general fermentable sugar, powder obtained from sunflower stalk is subjected to step 1) to yield a solid residue, and the solid residue is added with water or water and clay minerals to adjust the solid contents to 8%, which is then introduced into a high pressure reactor and subjected to a reaction at 190° C. for 5 minutes (see Korean Laid-open Patent Publication No. 2012-73087 and International Publication No. WO 2012/087068). At the said temperature, the yield rates of xylose and xylan, produced by hydrolysis of hemicellulose, would be maximized, but the amounts of furfural, prone to over-decomposition, and HMF, formed by over-decomposition of cellulose, would be minimized. Meanwhile, since the glucose yield from enzymatic saccharification after pretreatment is lower than that of enzymatic saccharification after vigorous pretreatment, the pretreatment technique which utilizes clay minerals during the enzymatic saccharification may be used (see Korean Laid-open Patent Publication No. 2012-73087 and International Publication No. WO 2012/087068) or polyethylene glycol (see U.S. Pat. No. 7,972,826).

In the third step of the present invention, i.e., the solid-liquid separation step, the pretreated biomass is subjected to solid-liquid separation to yield a solid residue containing a small amount of a liquid part. The solid-liquid separation step may be carried out by any conventional solid-liquid separation techniques known in the art, e.g., centrifugation, suction filtration, pressure filtration, and the like. The pretreated solid residue obtained from the solid-liquid separation process may contain a pretreated liquid part in an amount about 2 to 4 times the dried weight. Unlike conventional techniques that wash the pretreated solid residue with hot water, in the present method for preparing fermentable sugar, the pretreated solid residue is directly used in the following saccharification process which employs a cellulase complex enzyme. It is preferable to control the solid residue after the solid-liquid separation to have the pretreated liquid part in an amount of 5 to 30 wt % based on the total amount of the liquid part produced in the pretreatment process. Since the liquid part contains a sufficient amount of microbial growth inhibitors that can prevent microbial growth commonly caused by airborne contamination, e.g., lactic acid bacteria, around 50° C. which is the optimum temperature for cellulase activity. The present method has an advantage that the pretreated biomass can go through enzymatic saccharification for more than 72 hours without requiring a separate sterilization process. Also, the liquid part can maintain the sugar solution at 50° C. or higher during the enzyme recovery or removal process and the concentration process using a separation membrane after the enzymatic saccharification step, thereby preventing microbial contamination.

Once the pretreated liquid part is recovered by the solid-liquid separation step, it contains a small amount of xylose, large amounts of xylooligosaccharide, acetic acid, trace amounts of furfural and lignin degradation products. Also, most of the impurities are removed by step 1) of the present invention, and thus, the liquid part can be used as an excellent raw material for the production of xylitol or dietary fiber.

In the fourth step of the present invention, i.e., the enzymatic saccharification step, the solid residue obtained from step 3) is subjected to enzymatic saccharification at 45 to 55° C. under an acidic pH condition of 4.8 to 5.2. During this process, cellulose and hemicellulose contained in the pretreated biomass are converted to monosaccharides such as glucose and xylose.

In this process, the solid residue obtained from step 3) is added with a cellulase complex enzyme, and then water may also be added thereto for saccharification process. However, the amount of water is preferably limited so as to prepare a sugar solution in high yield after the saccharification process. Thus, the weight ratio of the solid residue to water in the enzymatic saccharification is, preferably, 1:3 to 1:10 based on the dried weight of the solid residue.

Cellulase complex enzyme containing hemicellulose is used for the saccharification of the pretreated biomass. Specific examples of the cellulase complex enzyme include Celluclast 1.5 L or a mixture of Celluclast Cone BG and Novozyme™ 188, a mixture of Cellic CTec2 and Cellic HTec2, a mixture of Cellic CTec3 and hemicellulase, Celluzyme, a mixture of Cereflo and Ultraflo (Novozymes, Denmark), Accellerase™, a mixture of Laminex and Spezyme (Genencor Int.), and Rohament (Rohm GmbH), and the like. Since the pretreated biomass contains a small amount of hemicellulose, hemicellulose may be added so as to promote the rate of hydrolysis reaction, and the mixing ratio of cellulase to hemicellulase is, preferably, about 9:1 to 10:0. Preferably, the cellulase complex enzyme is used in amount of 0.001 g to 0.5 g per 1 g of dried biomass weight.

The enzymatic saccharification is conducted under an optimal condition in which the activities of the hydrolyzing enzymes are maximized. Preferably, in case of a mixture of Cellic CTec2 and Cellic HTec2, the reaction is carried out at a pH of 4.8 to 5.2 and at 50±1° C., and the saccharification is maintained for 24 hours to 96 hours unless there is microbial contamination.

Since the pretreated liquid part contained in the solid residue that has been carried over to the enzymatic saccharification process contains substances which may inhibit hydrolases of cellulose, e.g., xylose and xylooligosaccharide, the sugar yield of the enzymatic saccharification may be lowered slightly. Thus, in order to improve the sugar yield in the enzymatic saccharification of the pretreated biomass, the present method may employ the following two methods known in the art. The first method employs polyethylene glycol (PEG) which is known to improve activities of cellulose hydrolase (see U.S. Pat. No. 7,972,826). This method can increase the sugar yield by inhibiting the irreversible adsorption of enzymes on lignin located on the surface of pretreated biomass. In this respect, PEG having a molecular weight of at least 30,000 is employed so that it can be recovered by separation membrane process after the saccharification and may not remain as an impurity. The second method employs a small amount of certain clay minerals during the autohydrolysis step or the enzymatic saccharification step (see Korean Laid-open Patent Publication No. 2012-73087 and International Publication No. WO 2012/087068). This method is advantageous for the manufacture of fermentable sugar since it can improve sugar yield without washing the pretreated solid residue with water, and the sugar solution obtained therefrom does not contain any additives.

In the fifth step of the present invention, i.e., the sugar solution recovery step, a sugar solution is recovered by repeating the solid-liquid separation and extraction using the saccharified material obtained in step 4). For this recovery process, various techniques such as batch type or continuous centrifugation, filter press or screw press may be used. In case of batch type centrifugation, for example, the saccharified material is centrifuged to yield a supernatant; the hydrolysis residue is diluted with water in an equal volume; the diluted hydrolysis residue is centrifuged to yield a sugar solution; and the centrifugation and recovery process is repeated 3 to 5 times to recover at least 99% of the sugar produced from the enzymatic saccharification.

In the sixth step of the present invention, i.e., the concentration step, the sugar solution obtained in step 5) is filtered and concentrated and impurities are removed from the solution. The sugar solution obtained in step 5) is diluted during the recovery process, and the final concentration of the sugar solution may become about 60 g/L to 150 g/L, which shows a 50% reduction from the initial concentration. This low concentration level can be increased by at least 30% via concentration process which utilizes membrane separation technique using a reverse osmosis membrane.

The concentration process may be carried out by various techniques known in the art, e.g., reverse osmosis, nanofiltration, and the like. Also, ultrafiltration may be used to recover enzymes contained in the sugar solution, or the enzymes may be removed by heating the solution to denature the enzymes and then separating the precipitate by solid-liquid separation technique.

The fermentable sugar obtained in step 6) of the present invention contains a high concentration of glucose in an amount of at least 30% to prevent microbial contamination, and also comprises low concentrations of organic acids such as acetic acid and formic acid which are hydrolysates of hemicellulose; trace amounts of furfural and HMF; phenolic compounds which are degradation product of lignin; and small amounts of inorganic salts derived from the biomass. Unlike the sugar concentration, however, the concentrations of these impurities are very low so that the sugar solution would not affect the growth and development of many microorganisms used in industrial fermentation once the sugar solution is diluted to a concentration level which generally allows normal production of metabolites.

Accordingly, the fermentable sugar obtained in step 6) of the present invention may be used in the culturing of various microorganisms used for industrial fermentation such as *Escherichia coli* and yeast which are most commonly used in the manufacture of various chemical substances and biofuels; *Clostridium acetobutylicum* and *Clostridium beijerinckii* which are used in the manufacture of butanol and acetone; *Lactococcus lactis* and *Lactobacillus* sp. which are used in the manufacture of lactic acid; and *Corynebacterium glutamicum* which is used in the manufacture of amino acids.

In the method for preparing fermentable sugar of the present invention, examples of lignocellulosic biomass include grassy biomass and woody biomass. Besides said lignocellulosic biomass, however, any biomass containing cellulose as its main sugar source, e.g., algal biomass including microalgae and marine algae, can also be used without limitation. Specific examples of grassy biomass include, but not limited to, trunk and frond of palm trees, empty fruit bunch, sunflower stalk, rice straw, barley straw, wheat straw, corn stalk, reed, silver grass, switchgrass, rape stalk, sweet sorghum stalk, sorghum stalk, cattail, and the like. Specific examples of woody biomass include, but not limited to, yellow poplar, willow, acacia, eucalyptus, spruce, and the like.

The method for preparing fermentable sugar from lignocellulosic biomass of the present invention allows the production of various industrial raw materials by employing the most simplified method through fractionation of biomass and also prepares fermentable sugar in high yields which can be effectively used in culturing various microorganisms for industrial fermentation, and thus, can maximize the utilization efficiency of the biomass.

Hereinafter, the present invention is described in greater detail. The following Examples are given for the purpose of illustration only, and are not intended to limit the scope of the present invention.

Example 1: Preparation of Fermentable Sugar from Sunflower Stalk 360 g (dry weight) of sunflower stalk powder of known ingredient composition was introduced into a cotton cloth bag, which was then heated for 10 minutes at 95° C. in a steamer containing 3,600 g of distilled water. Subsequently, the cotton cloth bag was placed in a centrifugal dehydrator to remove water. After the dewatering process, the cotton cloth bag was placed in a steamer containing 2,400 g of distilled water to absorb sufficient amount of water, which was then subjected to dewatering in a dehydrator.

The content from the cotton cloth bag was divided into three equal parts, placed in a reactor having a capacity of 2 L (Parr reactor, Parr Instrument Co. Ltd., U.S.A.), and distilled water was added thereto to make each part to have a weight of 1,500 g. The reactor was heated, and the biomass was subjected to autohydrolysis at 190° C. for 5 minutes. Upon the completion of the reaction, the reactor was placed in flowing tap water for rapid cooling, and then the content was placed in a cotton cloth bag. A total of 720 g of the biomass content was pretreated by repeating the above procedure five more times. The biomass content was collected, placed in a cotton cloth bag, and dewatered using a dehydrator. After the dewatering process, the resulting solid residue was placed in a fermentation tank of a fermenter (BioTron, Korea), which was added with nonionic water to make up a total weight of 4 kg.

72 g of diatomite powder (Rex Material, Co. Ltd., Pohang, Korea) was added thereto, followed by stirring. Then, 64.8 mL of Cellic CTec2 and 7.2 mL of Cellic HTec2 were added as cellulose hydrolases, and the mixture was stirred at 50±1° C., pH 5.0-10.1 and 150 rpm. An original sugar solution was prepared when the saccharification was completed three days after the initial reaction, and the amount of the saccharified material was measured. 1 mL of the solution was collected and used as a compositional analysis sample.

The saccharified material in the fermentation tank was transferred to a cotton cloth bag, which was then dewatered to recover a sugar solution. After recovering a sugar solution from the cotton cloth bag once, the cotton cloth bag was placed in a beaker containing 800 mL of distilled water to absorb water, refrigerated for at least 12 hours, and then dewatered to separate a sugar solution therefrom. This recovery process was repeated two more times to collect sugar solutions, and the sugar solutions were combined with the original sugar solution.

The resulting sugar solution was heated at 121° C. for 20 minutes to precipitate denatured enzymes, centrifuged and subjected to filtration using a filter paper to obtain a clear sugar solution. Subsequently, the resulting sugar solution was concentrated using a concentrator (manufactured by the inventor) equipped with a reverse osmosis membrane module (RE1812-80, Woongjin Corp., Korea) to yield a sugar solution having a glucose concentration of at least 300 g/L (hereinafter referred to as "fermentable sugar 1").

The fermentable sugar thus obtained was analyzed by using high performance liquid chromatography (HPLC, available from Waters) provided with an Aminex HPX-87H column (BioRad) and a refractive index detector to measure the glucose concentration, concentrations of other sugars and acetic acid, and yield rates were calculated therefrom. The concentrations of furfural and HMF were measured, and the yield rate of sugar solution before the concentration and the yield rate of fermentable sugar after the concentration are shown in Tables 2 and 3, respectively. Also, using the phenolic compounds extracted from the pretreated sunflower stalk as a standard, the fermentable sugar was diluted 200 times, and the absorbance value of the sample was measured at 320 nm using a spectrophotometer (Beckmann, Germany). The concentration of the phenolic compound calculated from the sugar solution is shown in Table 3. The amounts of inorganic salts included in the highly concentrated fermentable sugar were measured using a Plasma-Atomic Emission Spectrometer (ICP-AES, ThermoScientific, U.S.A.) and the total amount was recorded.

Comparative Example 1: Preparation of Sugar Solution from Sunflower Stalk Obtained by Washing Autohydrolyzed Material 120 g (dry weight) of the same kind of sunflower stalk powder used in Example 1 was introduced into a reactor having a capacity of 2 L (Parr reactor, Parr Instrument Co. Ltd., U.S.A.), and distilled water was added thereto to make the total weight of 1,500 g. Subsequently, the mixture was subjected to autohydrolysis at 190° C. for 5 minutes. Upon the completion of the reaction, the reactor was placed in flowing tap water for rapidly cooling, and then the content was placed in a cotton cloth bag. A total of 720 g of the biomass content was pretreated by repeating the above procedure five more times. The biomass content was collected, placed in a cotton cloth bag, and dewatered using a dehydrator.

After the dewatering process, the resulting solid residue was placed in 20 L of boiling water, which was then dewatered using a dehydrator. The pretreated solid residue was placed in a fermentation tank of a fermenter (BioTron, Korea), which was added with noninoic water to make up a total weight of 4 kg. 72 g of diatomite powder was added thereto, followed by stirring. Then, the fermentation tank was sealed and sterilized in an autoclave at 121° C. for 60 minutes.

As cellulose hydrolases, 64.8 mL of Cellic CTec2 and 7.2 mL of Cellic HTec2, were dissolved in 430 mL of ultrapure water, and the resulting solution was filtered through a filter system (Corning Inc., U.S.A.) equipped with 0.22 μm membrane filter, which was then added to a fermentation tank in a clean bench. The mixture was stirred at 150 rpm while maintaining the fermentation tank at 50±1° C. and pH 5.0±0.1.

In order to test contamination by lactic acid bacteria, the mixture was stirred for three days from the initiation of enzymatic hydrolysis reaction, and the amount of the saccharified material was collected at daily intervals. Samples were analyzed by using HPLC (Waters) provided with an Aminex HPX-87H column (BioRad) and a refractive index detector to calculate the yield rates of glucose and other sugars, lactic acid and acetic acid and to measure the concentrations of furfural and HMF. The results are shown in Table 2 below.

The saccharified material in the fermentation tank was transferred to a cotton cloth bag, which was then dewatered to recover a sugar solution. After recovering a sugar solution from the cotton cloth bag once, the cotton cloth bag was placed in a beaker containing 800 mL of distilled water to absorb water, refrigerated for at least 12 hours, and then dewatered to separate a sugar solution therefrom. This recovery process was repeated two more times to collect sugar solutions, and the sugar solutions were combined with the original sugar solution. The resulting sugar solution was heated at 121° C. for 20 minutes to precipitate denatured enzymes, centrifuged and subjected to filtration using a filter paper to obtain a clear sugar solution. The sugar solution was concentrated using a concentrator equipped with a reverse osmosis membrane module to yield a sugar solution having a glucose concentration of at least 300 g/L (hereinafter referred to as "fermentable sugar 2").

The fermentable sugar thus obtained was analyzed by using HPLC to measure concentrations of each ingredients including sugar. The results are shown in Table 3. Also, the concentrations of phenolic compounds and inorganic salts were measured by using the same method used in Example 1, and the results are shown in Table 3.

Comparative Example 2: Preparation of Fermentable Sugar from Sunflower Stalk without Removing Extractable Substances 120 g (dry weight) of the same kind of sunflower stalk powder used in Example 1 was introduced into a reactor having a capacity of 2 L (Parr reactor, Parr Instrument Co. Ltd., U.S.A.), and distilled water was added thereto to make the total weight of 1,500 g. Subsequently, the mixture was subjected to autohydrolysis at 190° C. for 5 minutes. Upon the completion of the reaction, the reactor was placed in flowing tap water for rapidly cooling, and then the content was placed in a cotton cloth bag. A total of 720 g of the biomass content was pretreated by repeating the above procedure five more times. The biomass content was collected, placed in a cotton cloth bag, and dewatered using a dehydrator.

After the dewatering process, the resulting solid residue was placed in a fermentation tank of a fermenter (BioTron, Korea), which was added with noninoic water to make up a total weight of 4 kg. 72 g of diatomite powder was added thereto, followed by stirring.

Then, 64.8 mL of Cellic CTec2 and 7.2 mL of Cellic HTec2 were added as cellulose hydrolases, and the mixture was stirred at 50±1° C., pH 5.0±0.1 and 150 rpm. An original sugar solution was prepared by stirring the mixture for three days from the initiation of enzymatic hydrolysis reaction. 1 mL sample was collected and used for compositional analysis.

The original sugar solution was analyzed by using HPLC (Waters) provided with an Aminex HPX-87H column (Bio-Rad) and a refractive index detector to calculate the yield rates of glucose and other sugars, lactic acid and acetic acid and to measure the concentrations of furfural and HMF. The results are shown in Table 2 below. The saccharified material in the fermentation tank was transferred to a cotton cloth bag, which was then dewatered to recover a sugar solution.

After recovering a sugar solution from the cotton cloth bag once, the cotton cloth bag was placed in a beaker containing 800 mL of distilled water to absorb water, refrigerated for at least 12 hours, and then dewatered to separate a sugar solution therefrom. This recovery process was repeated two more times to collect sugar solutions, and the sugar solutions were combined with the original sugar solution. The resulting sugar solution was heated at 121° C. for 20 minutes to precipitate denatured enzymes, centrifuged and subjected to filtration using a filter paper to obtain a clear sugar solution. The sugar solution was concentrated using a concentrator (manufactured by the inventor) equipped with a reverse osmosis membrane module to yield a sugar solution having a glucose concentration of at least 300 g/L (hereinafter referred to as "fermentable sugar 3").

The fermentable sugar thus obtained was analyzed by using HPLC to measure concentrations of each ingredients including sugar. The results are shown in Table 3. Also, the concentrations of phenolic compounds and inorganic salts are measured by using the same method as used in Example 1, and the results are shown in Table 3.

The preparation processes of Example 1 and Comparative Examples 1 and 2 are summarized in Table 1 below.

TABLE 1

|  | Example 1 | Comparative Example 1 | Comparative Example 2 |
|---|---|---|---|
| Removal of extractable substances from biomass by hot water extraction | Heated at 95° C. for 10 min and dewatered (Total 2 times) | — | — |
| Autohydrolysis | 190° C. for 5 min | 190° C. for 5 min | 190° C. for 5 min |
| Pretreated material treatment | Cooled and dewatered to remove the liquid part | Cooled and washed the solid residue with hot water | Cooled and dewatered to remove the liquid part |
| Sterilization of pretreated material | — | 121° C. for 60 min | — |
| Aseptic treatment using filtration | — | Filtering with 0.22 μm membrane | — |
| Enzymatic saccharification of solid residue | 50 ± 1° C., pH 5.0 ± 0.1, 150 rpm | 50 ± 1° C., pH 5.0 ± 0.1, 150 rpm | 50 ± 1° C., pH 5.0 ± 0.1, 150 rpm |
| Enzyme removal | Heated at 121° C. for 20 min and filtered | Heated at 121° C. for 20 min and filtered | Heated at 121° C. for 20 min and filtered |
| Concentration | Reverse osmosis membrane module | Reverse osmosis membrane module | Reverse osmosis membrane module |

TABLE 2

| | Yield (g/100 g) and amount produced | | |
|---|---|---|---|
| Components | Example 1 | Comparative Example 1 | Comparative Example 2 |
| Glucose | 29.6 | 26.3 | 30.3 |
| Other sugars | 8.5 | 6.9 | 9.8 |
| Acetic acid | 1.3 | 1.0 | 1.1 |
| Lactic acid | 0.0 | 0.1 | 0.0 |
| HMF | 0.01 | 0.00 | 0.02 |
| Furfural | 0.02 | 0.00 | 0.02 |

The sunflower stalk, which was used as a biomass in the present invention, contained 35.1 g of cellulose (glucose amount when all of the cellulose in the biomass is converted to glucose), 18.8 g of hemicellulose (monosaccharide amount when all of the hemicellulose in the biomass is converted to monosaccharide) and 4.5 g of acetic acid. As shown in Table 1 above, the sugar solution of Example 1 prepared by a method for preparing fermentable sugar of the present invention achieved a glucose yield of 29.6 g by continuing the enzymatic saccharification for 72 hours without lactic acid bacteria contamination, while producing almost no over-decomposed products of sugar. Also, this method allows a small amount of liquid part containing microbial inhibitors generated during the pretreatment to remain in the pretreated solid residue, and then introducing the liquid part to enzymatic saccharification. As a result, the present method can prevent lactic acid bacteria contamination without requiring a separate sterilizing process, thereby improving the sugar yield.

On the contrary, in case of Comparative Example 1 in which the pretreated solid residue was washed with water and introduced to enzymatic saccharification, the lactic acid production was observed 24 hours after the saccharification, and the concentration of lactic acid was increased drastically after 48 hours. Thus, the enzymatic saccharification was stopped after 48 hours. The reason for much smaller glucose yield rate of Comparative Example 1 as compared with that of the sugar solution of Example 1 was partly due to the shortened time of enzymatic saccharification. However, another reason is that some of the pretreated materials were lost as small particles during the washing process of the pretreated material. As such, washing the pretreated material with hot water may be used to remove over-decomposed products of sugar and lignin degradation products and may improve the purity of the sugar solution obtained from the enzymatic saccharification. However, it reveals that microbial contamination, e.g., lactic acid bacteria, during the enzymatic saccharification is unavoidable, thereby causing great difficulties in the industrial production of fermentable sugar.

Also, in case of Comparative Example 2 in which the biomass was directly pretreated and the solid residue obtained by subjecting the pretreated material to a solid-liquid separation was enzyme-saccharified, it showed the highest glucose yield rate of 30.3 g. This is because free sugars contained in the biomass were included in the sugar solution since the biomass was directly employed without going through a hot water extraction. However, such free sugars are prone to over-decomposition and, as can be seen in Table 2, can cause generation of HMF and furfural. Since these over-decomposition products are considered as impurities which must be removed for production of highly concentrated fermentable sugar for various microorganisms, this may become a critical factor that increases the costs of chromatography process in the following purification process.

TABLE 3

| | Compositions of the highly concentrated fermentable sugars (%) | | |
|---|---|---|---|
| Components | Example 1 (Fermentable sugar 1) | Comparative Example 1 (Fermentable sugar 2) | Comparative Example 2 (Fermentable sugar 3) |
| Glucose | 30.0 | 30.1 | 30.5 |
| Other sugars | 8.7 | 7.2 | 9.1 |
| Acetic acid | 0.6 | 0.5 | 0.4 |
| Lactic acid | 0.0 | 0.1 | 0.0 |
| HMF | 0.03 | 0.01 | 0.02 |
| Furfural | 0.02 | 0.00 | 0.01 |
| Phenolic compounds | 0.72 | 0.31 | 0.58 |
| Inorganic salts | 0.31 | 0.16 | 0.82 |

The compositions of the fermentable sugars obtained by concentrating the sugar solutions using a separation membrane, which were prepared from sunflower stalk after the autohydrolysis and enzymatic saccharification, are shown in Table 3. When the glucose concentration was adjusted to about 30%, the fermentable sugar 1 of the present invention and the fermentable sugar 3 of Comparative Example 2 both contain trace amounts of HMF and furfural but the fermentable sugar 2, which was prepared by washing the pretreated material with hot water followed by enzymatic saccharification, contained almost none of these substances. The concentrations of phenolic compounds in the fermentable sugar 1 of the present invention and the fermentable sugar 3 of Comparative Example 2 does not show much difference implying that these compounds were generated as a result of the pretreatment process. The fermentable sugar 2 of Comparative Example 1 which was prepared by washing the pretreated material with hot water also contained phenolic compounds. This indicates that phenolic compounds were released to the sugar solution during the enzymatic saccharification after washing with hot water suggesting that the effectiveness of washing is somewhat limited.

Suitable concentrations of such impurities contained in the pretreated material together with the enzymatic saccharification temperature of about 50° C. inhibit activities of lactic acid bacteria. The fermentable sugar 2 having small concentrations of HMF, furfural and phenolic compounds due to washing process is susceptible to contamination by lactic acid bacteria during the enzymatic saccharification, and thus, it contains lactic acid after the enzymatic saccharification.

One of the most noticeable features in Table 3 is the amount of inorganic salts. The fermentable sugar 3 in which hot water extraction process was omitted contained inorganic salts in an amount which is about 2.6 times greater than that of the fermentable sugar 1 of the present invention in which 90% of the extractable substances were removed from the biomass by hot water extraction. Such concentration level is considered extremely high compared to the concentration amounts of inorganic salts generally added for culturing industrial microorganisms. Thus, it is presumed that the inorganic salts may inhibit microbial growth depending on the type of the microorganisms.

Comparative Example 3: Comparison with Fermentable Sugar Prepared by Continuous Fractionation The present method is compared with a method which removes extractable substances by continuous fractionation as disclosed in Korean Laid-open Patent Publication No. 2011-0040367.

Example 2 and Experimental Example 1 of Korean Laid-open Patent Publication No. 2011-0040367 disclose a method for preparing fermentable sugar by removing hot water-extractable substances via continuous fractionation followed by autohydrolysis and enzymatic saccharification and the sugar yield as a result therefrom. The sugar yields of the fermentable sugar according to this method were 10.1 g for xylose and 28.2 g for glucose, per 100 g of dried sunflower. This result was a total sugar yield which combines the amount of the pretreated liquid part and the amount obtained from saccharification of the solid residue.

On the other hand, in Example 1 of the present invention, the sugar yields of a sugar solution obtained by pretreating the same biomass as the above method, and subjecting the pretreated solid residue which contained a liquid part in an amount of 30% or less to an enzymatic saccharification were 8.5 g for xylose and 29.6 g for glucose. When this xylose amount is added with 7.5 g of xylose amount which can be obtained by subjecting the liquid part collected from centrifugation of the pretreated material to enzymatic saccharification, the total xylose yield amounts to 16.0 g indicating that the present method is much more efficient than the prior method in terms of sugar yield. This is due to the fact that the recovery of liquid parts was incomplete when the hemicellulose from the sunflower stalk was hydrolyzed by continuous fractionation and the resulting liquid part was recovered through valves. In other words, this is because a considerable amount of hydrolysate of hemicellulose carried over to the following pretreatment process, as well as the loss of xylose at high temperature due to over-decomposition. Also, this may also cause generation of furfural, an over-decomposition product, in a large quantity and, thus, it is expected that high cost in distillation is incurred when the prior method was used for preparation of fermentable sugar.

Thus, it can be understood that the prior method which utilizes continuous fractionation of biomass is not an effective way for recovering liquid parts after pretreatment at a high temperature. Contrarily, the present invention utilizes more active solid-liquid separation techniques such as hot water extraction or pretreatment followed by centrifugation to achieve fractionation of biomass more effectively, thereby allowing production of fermentable sugar in the most cost-effective manner.

Experimental Example 1: Growth of Fermentation Strains Using Fermentable Sugars as Nutrient Source A culturing test of fermentation strains was conducted on the fermentable sugars 1 to 3 obtained in Example 1 and Comparative Examples 1 and 2.

Each of *E. coli* XB, *Lactobacillus paracasei* 13169 and *Clostridium beijerinckii* N8052 (pKBE4112ADH) was cultured in 2 mL of LB, MRS and 2YTG media, respectively, to prepare seed cultures.

Then, the fermentable sugars 1 to 3 were used, instead of glucose, to prepare each of P2, MR and LAB media. Specifically, P2 medium was prepared by adding 20 g/L of the fermentable sugar, 5 g/L of yeast extract, 1.5-fold amount of vitamins, 1.5-fold amount of inorganic salts and 1.5-fold amount of buffer solution; MR medium was prepared by adding 20 g/L of the fermentable sugar, 6.67 g/L of $KH_2PO_4$, 4 g/L of $(NH_4)_2HPO_4$, 0.8 g/L of citric acid, 5 mL/L of an aqueous solution of trace metals including trace amounts of iron sulfate, calcium chloride, zinc sulfate, manganese sulfate, copper sulfate, molybdenum salt and boron salt; and LAB medium was prepared by adding 20 g/L of the fermentable sugar, 5 g/L of polypeptone, 5 g/L of yeast extract, 0.1 g/L of sodium chloride, and 0.5 g/L of $MgSO_4$.

Subsequently, 0.2% of the seed was inoculated into each medium. *E. coli* XB and *Lactobacillus paracasei* 13169 were cultured under aerobic conditions at 37±1° C.; and *Clostridium beijerinckii* N8052 (pKBE4112ADH) was cultured under anaerobic conditions at 37±1° C. During the incubation, test samples were taken at 24 hour intervals (24, 48, 72 and 96 hours), and microbial growth of each sample was evaluated by measuring the optical density. Each sample was tested two times, and the test results were averaged.

Also, each medium was prepared by using glucose (for test use) to obtain a control group and the same test was conducted using such medium. The results are shown in Tables 4 to 6 below.

TABLE 4

Change in cloudiness of E. coli XB culture medium

| Incubation time | Control (glucose) | Fermentable sugar 1 | Fermentable sugar 2 | Fermentable sugar 3 |
|---|---|---|---|---|
| 0 | 0.05 | 0.39 | 0.37 | 0.63 |
| 24 | 2.30 | 2.69 | 1.98 | 0.63 |
| 48 | 2.21 | 3.47 | 2.82 | 1.28 |
| 72 | 2.33 | 3.63 | 3.01 | 1.91 |
| 96 | 2.36 | — | 3.28 | 2.03 |

TABLE 5

Change in cloudiness of Lactobacillus paracasei 13169 culture medium

| Incubation time | Control (glucose) | Fermentable sugar 1 | Fermentable sugar 2 | Fermentable sugar 3 |
|---|---|---|---|---|
| 0 | 0.20 | 0.46 | 0.55 | 0.48 |
| 24 | 2.23 | 5.87 | 6.54 | 6.35 |
| 48 | 2.54 | 6.88 | 7.50 | 6.86 |
| 72 | 2.70 | 7.09 | 7.86 | 6.57 |
| 96 | 2.80 | — | — | 7.77 |

TABLE 6

Change in cloudiness of Clostridium beijerinckii N8052 culture medium

| Incubation time | Control (glucose) | Fermentable sugar 1 | Fermentable sugar 2 | Fermentable sugar 3 |
|---|---|---|---|---|
| 0 | 0.03 | 0.26 | 0.27 | 0.53 |
| 24 | 1.30 | 0.45 | 0.31 | 0.54 |
| 48 | 2.38 | 2.84 | 0.34 | 1.29 |
| 72 | 3.50 | 3.03 | 0.34 | 2.87 |
| 96 | 3.31 | — | 0.34 | 3.13 |

As shown in Table 4 above, the growth of E. coli XB was more active in the fermentable sugar 1 than in the control which was prepared with glucose. E. coli XB also grew more actively in the fermentable sugar 2 which had a small amount of lactic acid as compared to the control, but it was less active than the fermentable sugar 1. In case of the fermentable sugar 3 which contained the largest amounts of inorganic salts and impurities, the growth activity was less active than that of the control.

Meanwhile, as can be seen in Table 5, Lactobacillus paracasei 13169 was very insensitive towards impurities, and thus, grew well in all fermentable sugars.

On the other hand, as shown in Table 6, Clostridium beijerinckii N8052 exhibited almost no growth in the fermentable sugar 2 which contained a small amount of lactic acid whereas the growth activity in the fermentable sugar 1 was almost the same as that of the control. Also, the growth activity of in the fermentable sugar 3 which had the largest amounts of inorganic salts was slightly slower than that of the fermentable sugar 1 according to the present invention.

What is claimed is:

1. A method for preparing fermentable sugar from lignocellulosic biomass for use in fermentation of industrial microorganisms, consisting of the steps of:
   1) adding water to coarsely ground or powder lignocellulosic biomass having an average particle diameter of 0.1 mm to 50 mm or powdered lignocellulosic biomass to produce a first mixture, heating the mixture at 95 to 140° C. for 1 to 60 minutes, and then dewatering the mixture before the first mixture cools down to produce a first solid residue;
   2) adding water to the solid residue obtained in step 1), and subjecting the mixture to autohydrolysis pretreatment at 170 to 210° C. for 1 to 30 minutes;
   3) subjecting the autohydrolyzed material obtained in step 2) to solid-liquid separation to obtain a solid residue containing an amount of 5 to 30 wt % based on the total amount of the liquid part of the autohydrolyzed material produces in the pretreatment process;
   4) subjecting the solid residue obtained in step 3) to enzymatic saccharification at a temperature of 45 to 55° C. using a cellulase complex enzyme;
   5) repeating solid-liquid separation and extraction using the saccharified material obtained in step 4) to obtain a sugar solution; and
   6) subjecting the sugar solution obtained in step 5) to filtration, concentration and then impurity removal.

2. The method of claim 1, wherein the weight ratio of the coarsely ground or powder lignocellulosic biomass having an average particle diameter of 0.1 mm to 50 mm or powdered lignocellulosic biomass to water in step 1) is in a range of 1:4 to 1:20.

3. The method of claim 1, wherein the solid-liquid separation in step 3) is carried out by centrifugation, suction filtration or pressure filtration.

4. The method of claim 1, wherein the recovery of the sugar solution of step 5) is carried out by batch type or continuous centrifugation, filter press or screw press.

5. The method of claim 1, wherein the filtration, concentration and impurity removal of the sugar solution in step 6) are carried out by a membrane separation technique using a reverse osmosis membrane.

6. The method of claim 1, wherein the fermentable sugar obtained in step 6) contains glucose in an amount of at least 30%.

* * * * *